(12) United States Patent
Ashok et al.

(10) Patent No.: US 10,444,215 B2
(45) Date of Patent: Oct. 15, 2019

(54) METHOD AND DEVICE FOR ANALYZING ALCOHOLIC BEVERAGES

(71) Applicant: University Court of the University of St Andrews, St Andrews (GB)

(72) Inventors: Praveen Cheriyan Ashok, Dunfermline (GB); Gajendra Pratap Singh, Fife (GB); Kishan Dholakia, Fife (GB)

(73) Assignee: University Court of the University of St Andrews, St Andrews (GB)

( * ) Notice: Subject to any disclaimer, the term of this patent is extended or adjusted under 35 U.S.C. 154(b) by 0 days.

(21) Appl. No.: 15/355,352

(22) Filed: Nov. 18, 2016

(65) Prior Publication Data
US 2017/0138919 A1 May 18, 2017

Related U.S. Application Data

(63) Continuation of application No. 14/861,570, filed on Sep. 22, 2015, now Pat. No. 10,222,362, which is a (Continued)

(30) Foreign Application Priority Data

Sep. 28, 2010 (GB) .................................. 1016270.9

(51) Int. Cl.
*G01N 33/14* (2006.01)
*G01N 21/64* (2006.01)
(Continued)

(52) U.S. Cl.
CPC ...... *G01N 33/146* (2013.01); *B01L 3/502715* (2013.01); *B01L 3/502784* (2013.01);
(Continued)

(58) Field of Classification Search
CPC .... G01N 21/65; G01N 21/651; G01N 21/653; G01N 21/655; G01N 21/656;
(Continued)

(56) References Cited

U.S. PATENT DOCUMENTS 5,302,272 A 4/1994 Klein
5,604,587 A 2/1997 Che et al.
(Continued)

FOREIGN PATENT DOCUMENTS

| EP | 616211 A1 | 1/1999 |
| EP | 1182443 A2 | 2/2002 |
| WO | 2010007371 A2 | 1/2010 |

OTHER PUBLICATIONS

Leonardo S. Mendes, Flavia C.C. Oliveira, Paulo A.Z. Suarez, Joel C. Rubim, "Determination of ethanol in fuel ethanol and beverages by Fourier transform (FT)-near infrared and FT-Raman spectrometries," Analytica Chimica Acta 493 (2003) 219-231.*
(Continued)

*Primary Examiner* — Violeta A Prieto
(74) *Attorney, Agent, or Firm* — Moore & Van Allen PLLC; W. Kevin Ransom

(57) ABSTRACT

A Raman spectroscopic detection device comprising at least one microfluidic sample channel; at least one excitation waveguide for exciting a Raman signal and at least one collection waveguide for collecting a Raman signal. The output of the excitation waveguide and the input of the collection waveguide are positioned directly in the microfluidic sample channel.

18 Claims, 11 Drawing Sheets

Related U.S. Application Data continuation of application No. 13/818,501, filed as application No. PCT/GB2011/001406 on Sep. 28, 2011, now abandoned.

(51) Int. Cl.
*G01N 21/05* (2006.01)
*G01N 21/65* (2006.01)
*B01L 3/00* (2006.01)
*G01J 3/02* (2006.01)

(52) U.S. Cl.
CPC ............ *G01J 3/0218* (2013.01); *G01N 21/05* (2013.01); *G01N 21/64* (2013.01); *G01N 21/645* (2013.01); *G01N 21/65* (2013.01); *B01L 2200/027* (2013.01); *B01L 2200/0673* (2013.01); *B01L 2300/0627* (2013.01); *B01L 2300/0654* (2013.01); *B01L 2300/0816* (2013.01); *B01L 2300/0883* (2013.01); *B01L 2300/16* (2013.01); *G01N 2021/651* (2013.01); *G01N 2201/0846* (2013.01)

(58) Field of Classification Search
CPC .... G01N 21/658; G01N 33/14; G01N 33/143; G01N 33/146; G01N 33/2852
See application file for complete search history.

(56) References Cited

U.S. PATENT DOCUMENTS

| | | | |
|---|---|---|---|
| 5,736,410 A | 4/1998 | Zarling et al. | |
| 5,862,273 A | 1/1999 | Pelletier | |
| 6,020,207 A | 2/2000 | Liu | |
| 6,166,804 A | 12/2000 | Potyrailo et al. | |
| 6,571,118 B1 | 5/2003 | Utzinger et al. | |
| 6,825,928 B2 | 11/2004 | Liu et al. | |
| 6,870,165 B2 | 3/2005 | Amirkhanian | |
| 6,907,149 B2 | 6/2005 | Slater | |
| 8,638,431 B2 | 1/2014 | Ashok et al. | |
| 10,222,362 B2* | 3/2019 | Ashok | B01L 3/502715 |
| 2004/0152992 A1 | 8/2004 | Zeng | |
| 2004/0197043 A1 | 10/2004 | Cyr et al. | |
| 2007/0038123 A1 | 2/2007 | Fulghum | |
| 2007/0048746 A1 | 3/2007 | Su et al. | |
| 2007/0133984 A1* | 6/2007 | Maier | G01J 3/28 398/26 |
| 2007/0146704 A1 | 6/2007 | Schmidt et al. | |
| 2007/0147728 A1 | 6/2007 | Schmidt et al. | |
| 2007/0262265 A1 | 11/2007 | MacCraith et al. | |
| 2008/0123095 A1 | 5/2008 | Hubner et al. | |
| 2008/0221457 A1* | 9/2008 | Zeng | A61B 5/0071 600/477 |
| 2010/0110423 A1 | 5/2010 | Villaumie | |
| 2012/0075627 A1 | 3/2012 | Ashok et al. | |
| 2012/0089030 A1 | 4/2012 | Guze et al. | |
| 2012/0276549 A1 | 11/2012 | Cunningham et al. | |
| 2012/0309080 A1 | 12/2012 | Cunningham et al. | |
| 2013/0131488 A1* | 5/2013 | Zeng | A61B 5/0071 600/408 |
| 2013/0222799 A1* | 8/2013 | Ashok | B01L 3/502715 356/301 |
| 2016/0084766 A1* | 3/2016 | Ashok | B01L 3/502715 422/82.11 |
| 2017/0109598 A1* | 4/2017 | Lee | G01N 21/65 |

OTHER PUBLICATIONS

Frausto-Reyes et al. "Qualitative study of ethanol content in tequilas by Raman spectroscopy and principal component analysis," Spectrochimica Acta Part A 61 (2005) 2657-2662.*
Ashok, P. C. et al.: "Fiber probe based microfluidic raman spectroscopy"; Optics Express, Vol; Optics Express, vol. 18, No. 8; Apr. 12, 2010, pp. 7642-7649.
Ashok, P. C. et al.: "Waveguide confined Raman spectroscopy for microfluidic interrogation", published online 11, published online Jan. 11, 2011, Lab Chip, 11, pp. 1262-1270.
International Search Report for PCT/GB2011/001406, dated Nov. 18, 2011.
Lin, Cheng-Hsiang et al.: "Surface-enhanced Raman scattering microchip fabricated by femtosecond laser"; Optics Letters, vol. 35,; Optics Letters, vol. 35, No. 17, Sep. 1, 2010, pp. 2937-2939.
Nordon, Alison et al.: "Comparison of non-invasive NIR and Raman spectrometries for determination of alcohol content of spirits"; Analytica Chimica Act; Analytica Chimica Acta, vol. 548, No. 1-2, Aug. 29, 2005, pp. 148-158.
NPL Examination Report from European Patent Office for EP11767742.7 dated Mar. 22, 2016.
Search Report issued in GB1016270.9, dated Dec. 14, 2010.
RP photonics encyclopedia, waveguide, https://www.rp-photonics.com/waveguides.html.

* cited by examiner

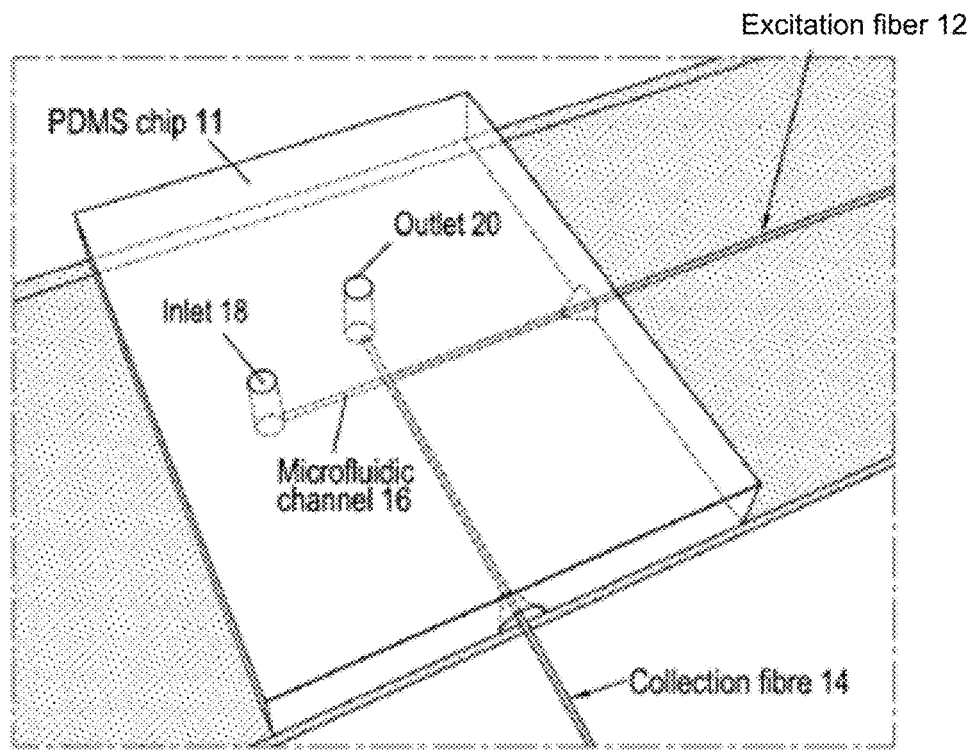
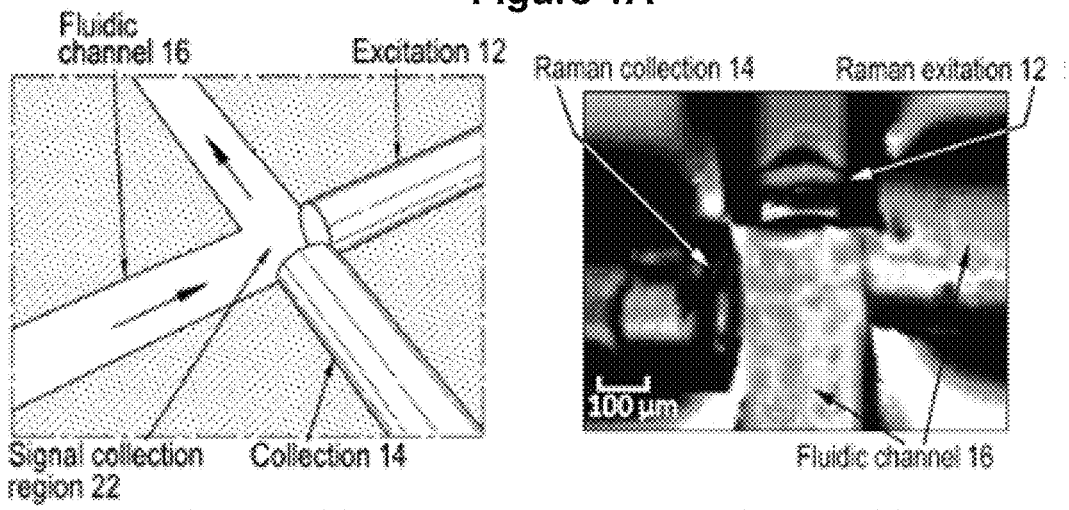
Figure 1A
Figure 1B
Figure 1C

METHOD AND DEVICE FOR ANALYZING ALCOHOLIC BEVERAGES

CROSS-REFERENCE TO RELATED APPLICATION(s)

This is a continuation of U.S. patent application Ser. No. 14/861,570, with a filing date of Sep. 22, 2015, which, in turn, is a continuation of U.S. patent application Ser. No. 13/818,501, with a filing date of Feb. 22, 2013, which in turn, claims priority to International Application PCT/GB2011/001406, with an international filing date of Sep. 28, 2011, which, in turn, claims priority to application number GB 1016270.9, with a filing date of Sep. 28, 2010; all of which are hereby incorporated herein by reference.

FIELD OF THE INVENTION

The present invention relates to a localized Raman spectroscopic detection system that has waveguides embedded in a device, for example a microfluidic device. The physical layout of the device localizes the sample to be interrogated and the embedded waveguides localize the excitation and collection of the Raman signal.

BACKGROUND OF THE INVENTION

Raman spectroscopy is a powerful and effective tool for analytical studies of biological and chemical samples. Raman scattering is inelastic light scattering from a sample that may yield a molecular fingerprint of the constituent molecules. However, an inherent limitation of this technique is the low Raman cross section of bio-molecules. Hence, long integration times are required to obtain a good signal to noise ratio. Nevertheless, Raman spectra have rich information content and a single Raman spectrum can provide information about all the molecular constituents of the sample.

Raman spectroscopy has numerous areas of application. For example, it has been used to analyze whisky, see for example A. Nordon, A. Sills, R. T. Burn, F. M. Cusick, and D. Littlejohn "Comparison of non-invasive NIR and Raman spectrometries for determination of alcohol content of spirits," Analytica Chimica Acta 548, 148-158 (2005). This study compares NIR spectroscopy with Raman spectroscopy, and concludes that Raman spectroscopy performs better for concentration calibration. However, the authors raise concerns about implementing a laser based Raman spectroscopic detection technique in a production line using free-space Raman detection devices. Also typical Raman acquisition times range from 10s of seconds to several minutes and require sample volumes in the range of milliliters.

Raman spectroscopy has been combined with microfluidic systems. To overcome the limitation of the inherently low Raman cross section, Surface Enhanced Raman Spectroscopy (SERS) based detection schemes have been employed in microfluidic systems. Other experiments have used confocal Raman microscopy for online monitoring of chemical reactions. In all these applications, monitoring is performed using a bulk Raman microscope and a microfluidic chip. However, using microscope based systems to collect Raman data from microfluidic chips can cause problems, because the signal is acquired through a substrate which has its own background signal. This limits the detection efficiency of the system. Using a microscope also precludes miniaturization.

There are two major issues when Raman spectroscopy is used in microfluidics: intensity of the Raman spectra and the background from the substrate of microfluidic chip. The former issue can be addressed using long acquisition times, SERS based detection approaches etc. The latter issue can be addressed by using a fused silica glass based microfluidic chip, which would have reduced fluorescence background and no Raman peaks in the fingerprint region. Alternatively, confocal detection schemes could be used to avoid background from the substrate. However, this results in comparatively higher acquisition time ranging from 10s of seconds to several minutes.

The article "Fibre Probe Based Microfluidic Raman Spectroscopy" by Ashok et al, Optics Express, Vol. 18, No. 8, 29 Mar. 2010 describes a fiber probe embedded in fluidic channels for Raman detection. This method allows in situ probing of an analyte in a fluidic channel, fabricated using microfluidic fabrication techniques, and so avoids any background from the substrate in the collected Raman spectra. However, the fluidic channel size of such devices is in the millimeter scale, and so it is not feasible to integrate this detection scheme in microfluidic chips whose channel dimensions are in micrometer scales.

SUMMARY OF THE INVENTION

According to the present invention, there is provided a microfluidic device comprising at least one sample channel; at least one excitation waveguide for exciting a Raman signal and at least one collection waveguide for collecting a Raman signal, wherein the at least one excitation waveguide is positioned so that its output end is in the sample channel and the at least one collection waveguide is positioned so that its input end is in the at least one sample channel.

The excitation and collection waveguides are embedded in the microfluidic channel to excite and collect the Raman signal. The ends of the waveguides extend directly into the channel, so that they can contact a sample therein. No discrete or separate optical elements lie between the end of the excitation waveguide and the sample to modify the output beam profile from the waveguide. Equally, no discrete or separate optical elements lie between the end of the collection waveguide and the sample to modify the beam profile from the sample.

By using waveguides without any optical elements at their ends, the relative distance between the ends of the excitation and collection waveguides is of the order of the size of the core of the waveguide. This results in localized excitation and collection of Raman signal from the close vicinity of the end of the waveguide, maximizing the collection efficiency of the Raman signal.

Since the output beam from the waveguide is diverging, by ensuring the cross sectional area of the waveguide is same as that of the microfluidic channel, the whole cross section of the microfluidic channel is interrogated in this detection approach. This helps to achieve sampling of maximum available volume of the sample in the detection region, thereby increasing the sensitivity of detection. The microfluidic dimension of the channels allows interrogating very low sample volumes.

The embedded waveguides of the invention allow alignment free Raman detection. The sample that has to be interrogated only needs to be injected into the microfluidic channel Hence, the device of the invention can be used for analyte detection with minimal sample preparation and optical alignment.

The excitation and/or collection waveguide may be an optical fiber. In particular, the excitation and/or collection waveguide may be a multimode optical fiber. With the choice of fiber with different physical dimensions or with the choice of waveguides that can be fabricated with different physical dimensions, the detection scheme is scalable to be adapted to a wide range of microfluidic dimensions. Hence, this scheme could easily be integrated with other functional microfluidic designs.

The excitation and/or collection waveguide may be embedded in a material that forms a main body of the device.

The distance between the end of excitation and collection waveguides may be of the order of the size of the core of each waveguide.

The sample channel may be at least part of a microfluidic channel that allows fluid to flow therethrough.

The size of the sample/microfluidic channel may be <500 μm.

The ends of the excitation waveguide and the collection waveguide define the sample detection volume.

The device may be integrated with one or more functional microfluidic devices, for example a microfluidic device adapted to generate micro-droplets and/or a microreactor for allowing one or more reactions to occur within the device.

The excitation waveguide and the collection waveguide may be mutually orthogonal.

The sample/microfluidic channel, the excitation waveguide and the collection waveguide may have substantially the same peripheral dimensions.

The sample/microfluidic channel, the excitation waveguide and the collection waveguide are arranged in a cross configuration.

The sample/microfluidic channel and one of the excitation waveguide and the collection waveguide may be arranged in a T configuration.

Means may be provided for causing fluid to flow through the device. For example, a pump may be used to cause fluid flow. The pump may be a syringe pump. The pump may be manually activated or may be mechanically driven.

The device of the invention has a low volume sample chamber and is alignment-free. It can be used to analyze any fluid, for example biological fluids. As another example, the invention can be used for Scotch whisky analysis. By harnessing the advantages of optofluidics, the invention offers portability and fast detection with relatively low acquisition time (2 s) and very low sample volume (20 μl). Also, samples can be analyzed without any special sample preparation stage. This is particularly advantageous for the analysis of whisky.

BRIEF DESCRIPTION OF THE DRAWINGS

Various aspects of the invention will now be described by way of example only and with reference to the accompanying drawings, of which:

FIG. 1A, FIG. 1B, and FIG. 1C show various views of an integrated microfluidic fiber based Raman device for localized Raman spectroscopy;

DETAILED DESCRIPTION OF THE DRAWINGS

Figure 2A:
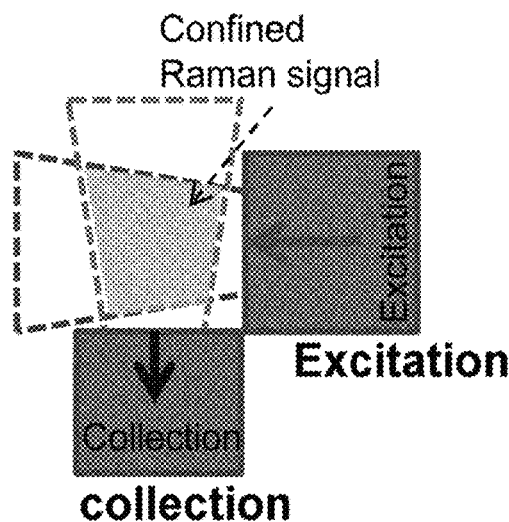
FIG. 2A shows the collection volume for the device of FIG. 1A.

FIGS. 1A-1C show a microfluidic device 10 that has a microfluidic chip 11 with embedded waveguides 12 and 14 adapted for highly localized measurements. This has an L-shaped microfluidic channel 16 with an input 18 and an output 20 for allowing fluid flow. In the example shown in FIG. 1A, the embedded waveguides are an embedded excitation fiber 12 having a divergent output for exciting a Raman signal and an embedded collection fiber 14 for collecting the Raman signal. The microfluidic channel 16, the excitation fiber 12 and the collection fiber 14 are mutually orthogonal.

Each of the excitation fiber 12 and the collection fiber 14 terminates directly in the microfluidic channel 16. Neither of the excitation fiber 12 and the collection fiber 14 has any optical element at its end or between its end and the microfluidic channel 16. Instead the exposed, filterless, fiber ends open directly into the microfluidic channel 16. The excitation fiber 12 and the collection fiber 14 are not part of a conventional probe assembly, but instead are directly embedded in the device 10. Hence, the outer surface of each fiber is in direct contact with the device 10. This help minimizes the size of the overall device. To minimize the sample and collection volumes, the excitation fiber 12, the collection fiber 14 and the microfluidic channel 16 are all sized to have substantially the same peripheral dimension and are arranged in a cross configuration, with the sample volume 22 defined at the junction of the fiber ends and the microfluidic channel.

Figure 2B:
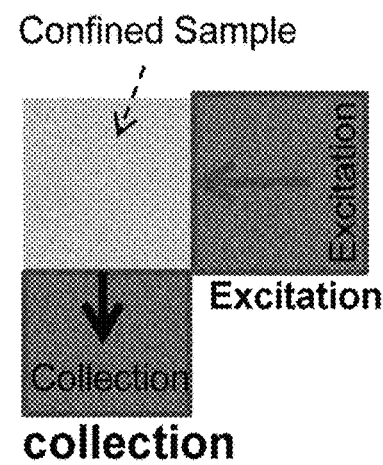
FIG. 2B shows the sample volume for the device of FIG. 1A.

The device 10 of the invention is based on two concepts of localization. The first localization is of the Raman collection. For an OH multimode fiber with a core size 200 μm, the output diverges at an angle 12.7°. For a length <200 μm, the beam size is comparable to the size of the core, beyond which the power density drops significantly. Hence, it is important to collect the Raman signal from a region as close as possible to the end of the excitation fiber 12. The same applies for the collection fiber 14 for maximum collection efficiency. FIG. 2A shows how the maximum overlap of excitation and collection is achieved by collecting the signal right from the end of the fiber. The second aspect of localization relates to the sample. Because of the localized signal collection, the sample being interrogated can be localized. Since the channel size is typically of the order of 100 μm-200 μm, the required sample volume 22 is minimal as shown in FIG. 2B.

Since a diverging beam is used for excitation, the whole cross section of the microfluidic channel is interrogated, in contrast to systems where a focused beam is used for confocal or non-confocal means of detection. Since the volume of interrogation is larger, the overall power density seen by the analyte is lower. Hence higher power can be used, keeping a low power density, thereby reducing the required acquisition time compared to confocal systems.

The microfluidic chip 11 is fabricated using soft lithography in PDMS. In order to embed optical fiber into the chip, fiber insertion channels are defined in the mold for the microfluidic chip 11. This can be done by placing a piece of fiber on the silicon substrate, on which the mold is fabricated, and by fixing it using UV curable adhesive (Norland). A negative photoresist (SU8, Microchem) was used to define the other microfluidic channels. To combine the channels defined by the fiber and the channel defined by photoresist, the photoresist was spun on top of the silicon substrate and SU8 channels were defined on the substrate using photolithography in such a way that the SU8 channel is physically connected to the fiber stuck on the mold. Once the mold was ready, the PDMS chip was fabricated using soft lithography and then the excitation and collection fibers were inserted into the chip as shown in FIG. 1A. Since the fiber insertion channel is predesigned for the desired collection geometry, the alignment requirement is minimal while inserting the fiber into the channel.

Various experiments have been conducted on the device 10 of FIG. 1A. For most of these (except the experiments investigating the impact of core size), the Raman signal was excited and collected using low OH multimode fibers with core size 200 μm (Polymicro Technologies, Arizona, USA). A laser of wavelength 785 nm (Laser2000 (UK) Ltd., Maximum power ~450 mW) was used for Raman excitation. The laser was coupled into the optical fiber through an SMA connector and the other end of the fiber was embedded into the microfluidic chip for Raman excitation. The tip of the collection fiber is coupled to a spectrometer (Shamrock SR-303i, Andor Technology) through a telescopic system to match the F-number of the fiber to that of the spectrometer. A long-pass filter (cut off wavelength 795.2 nm, Semrock, Inc. USA) was incorporated between the two lenses of the telescope to filter out the Rayleigh scattered photons. The spectrometer employed a 400 lines/mm grating and was equipped with a deep depletion back-illuminated and thermoelectrically cooled CCD camera (Newton, Andor Technology) for the detection of Raman signal. The resolution of the Raman system was measured by the FWHM of the silicon Raman peak at 520 $cm^{-1}$ and was found to be better than 6 $cm^{-1}$.

To investigate the performance of the device 10 of FIG. 1A, ethanol (Sigma Aldrich) was taken as a model analyte. The effects of three parameters—length, relative angle and core size of excitation and collection fibers 12 and 14—on collection efficiency of the Raman signal and fluorescence background were studied. For these studies, the power of the laser was fixed at 200 mW. For each data point, 20 Raman spectra of ethanol were collected with an acquisition time of 2 s.

Figure 3:
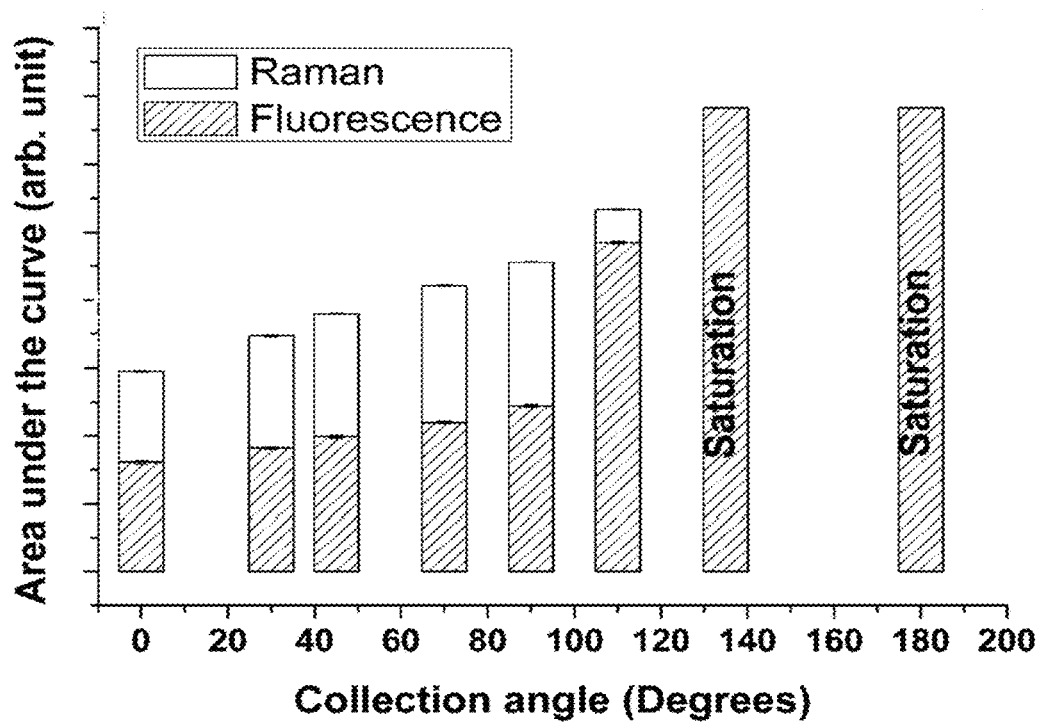
FIG. 3 is a is a plot of the area under the Ethanol Raman peak as a function of angle of collection.

The collection efficiency and fluorescent background depends strongly on the angle of collection. The effect of the relative angle between the excitation and collection fibers 12 and 14 was studied using the Ethanol peak at 884 $cm^{-1}$ as the reference peak. FIG. 3 shows the variation of peak intensity and fluorescent background for different angles of collection. It can be seen that the collection efficiency is maximum for 90° collection angle. For a collection angle of >90°, the collection fiber 14 collects more fluorescent background and Rayleigh scattered photons from the excitation fiber. Hence, the fluorescent background increases significantly leading to saturation of the CCD for higher collection angles. For collection angles of <90° the overlap between the excitation and collection volumes decreases, thereby reducing the net collection efficiency. Hence, an orthogonal collection geometry was used for further investigations.

Figure 4A:
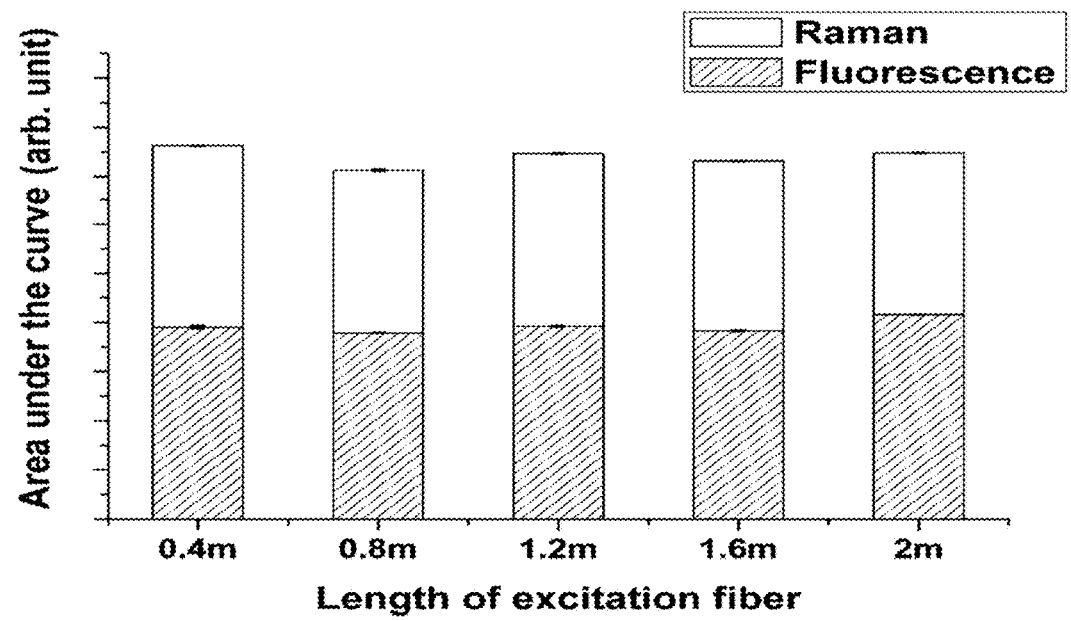
FIG. 4A and FIG. 4B are plots of the area under the Ethanol Raman peak as a function of fiber length.
Figure 4B:
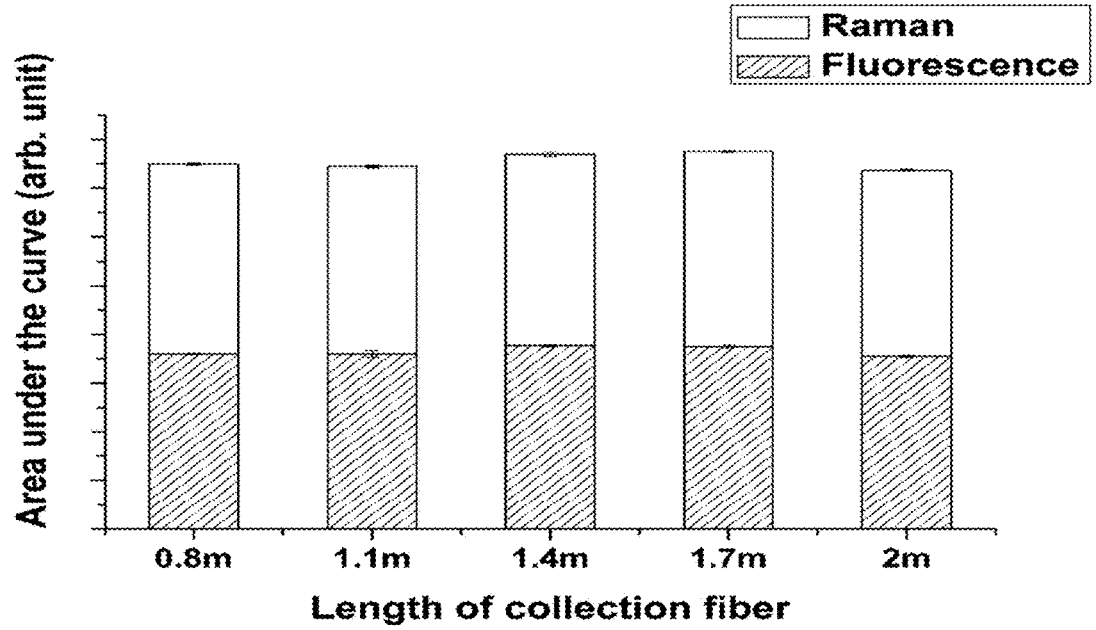

The effect of the length of the fiber to the Raman spectra was studied by varying the length of the excitation and collection fibers 12 and 14 using Ethanol peak at 884 $cm^{-1}$ as the reference peak. The results are shown in FIGS. 4A-4B. From this, it can be seen that the fluorescence background does not vary with the length of the fiber. This is because, at orthogonal geometry, the majority of the fluorescence background coming from the excitation fiber would not be collected by the collection fiber. Also, at this collection geometry a minimum amount of Rayleigh scattered excitation photons would be collected by the collection fiber, so that the fluorescence in the collection fiber would be minimum. Hence, at orthogonal collection geometry, the length of the excitation and collection fibers does not affect the Raman signal.

Figure 5:
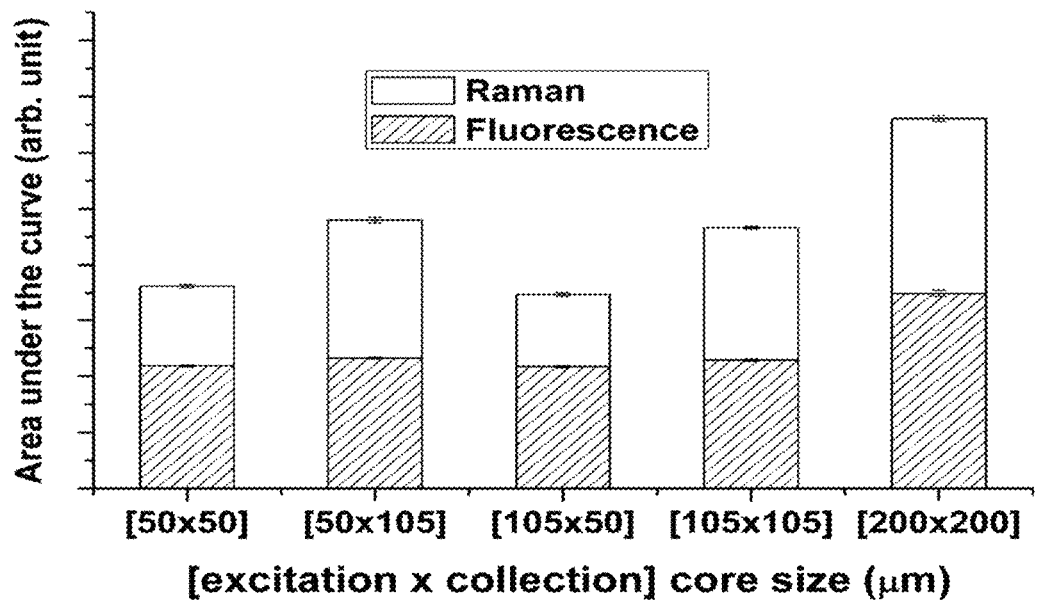
FIG. 5 is a plot of the area under the Ethanol Raman peak as a function of fiber core size.

The effect of core size was studied by collecting the Raman spectra of ethanol using low OH multimode fibers of different core sizes keeping the power of excitation constant. FIG. 5 shows the variation of peak intensity and fluorescent background as a function of core size. From this, it can be seen that the collection efficiency is mainly affected by the parameters of the collection fiber. There is no variation in the collection efficiency when the core size of the excitation fiber 12 was varied, keeping the core size of the collection fiber constant. Also, it can be seen that the collection efficiency is comparable for 200 μm (250 μm cladding diameter) core size fiber and 100 μm (125 μm cladding diameter) core size fiber. This demonstrates the scalablity of the device, which can be readily adapted to a range of microfluidic dimensions.

Figure 6:
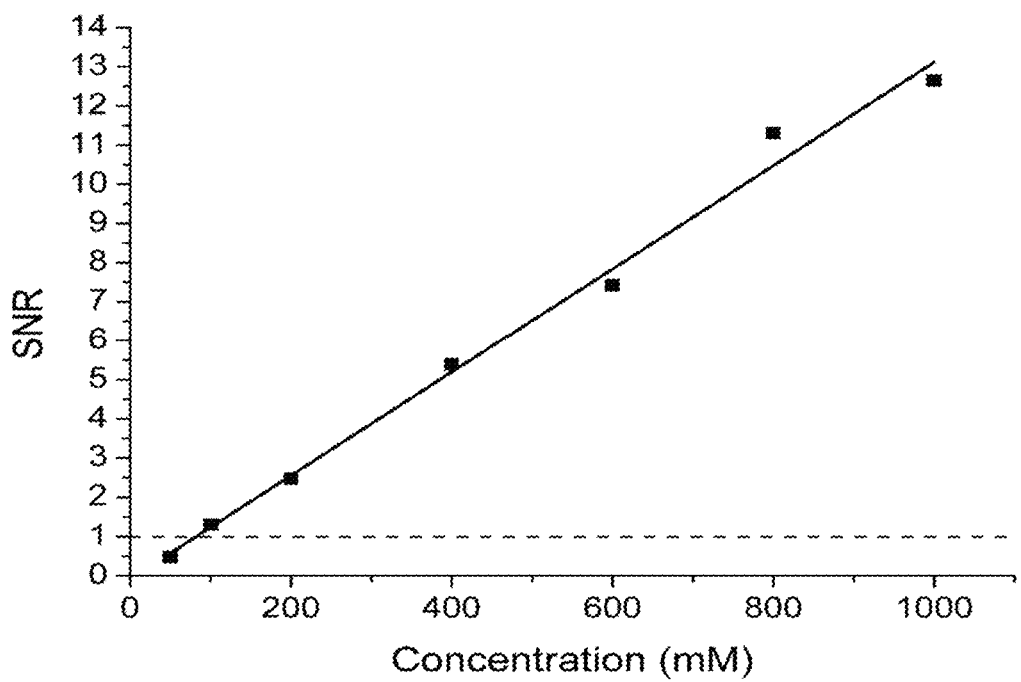
FIG. 6 is a plot of concentration vs signal to noise ratio for Raman spectra of urea.

To compare the performance of the device of the invention to its fiber probe counterpart (that has filters at the end of the fibers), the minimum detection limit of urea was calculated. The results of this are shown in FIG. 6. In FIG.

6, the dotted horizontal line corresponds to the level where the SNR=1. The intersection of the dotted line with the line that corresponds to the variation of SNR with concentration provides the Noise Equivalent Concentration or minimum detection limit of this system with given parameters.

From FIG. 6, it can be seen that the Noise Equivalent Concentration (NEC) was estimated to be 80 mM which is better than the probe based system. Even though there are filters at the probe head of the probe based system, there would be an insertion loss at the probe head due to the throughput (Etendue) mismatch between the probe head and the collection fiber, resulting in the reduction of sensitivity of the system. There is a tradeoff between the net collection efficiency of the system and fluorescent background. In the device of the invention, the absence of filters at the tip of the fiber results in increased fluorescent background. However, since the Raman signal is being collected directly to the collection fiber, there is no throughput mismatch. It can be seen from the NEC calculation that even though the fluorescent background is high, the minimum detection limit is better for compared to the conventional probe based system.

Figure 7:
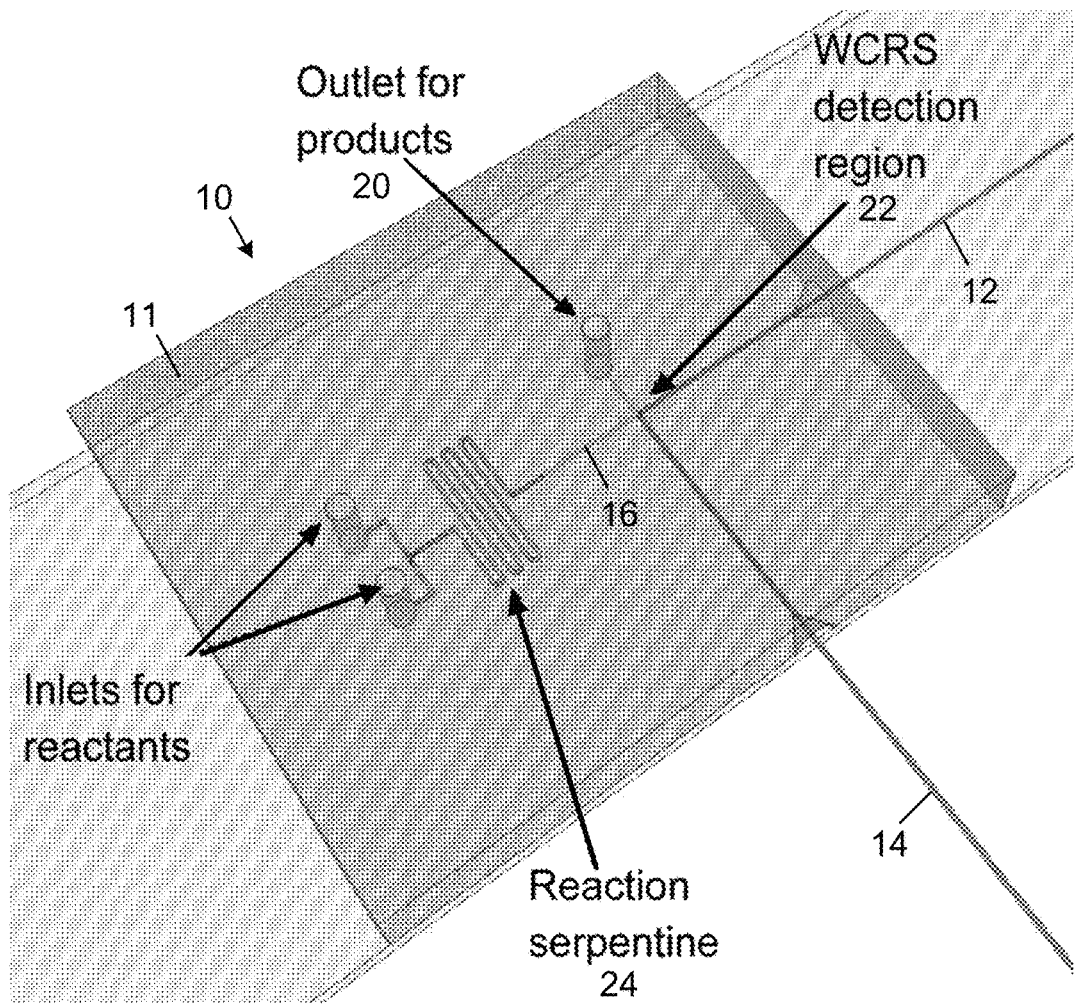
FIG. 7 is a view of a micro-reactor integrated with the device of FIG. 1A.

FIG. 7 shows the device of FIG. 1A integrated with a serpentine microreactor 24. This arrangement allows the dynamics of a chemical reaction to be monitored using Raman techniques. The serpentine microreactor 24 is designed for a binary reaction. As a specific example, the serpentine microreactor 24 has a microfluidic channel of rectangular cross section with 150 μn width and 60 μm height. The serpentine region widens into a microfluidic channel with circular cross section with diameter 250 μm. This channel is linked to the microfluidic channel 16 of the localized Raman device 10 of FIG. 1A. Reactants are input via two or more inlets and enter the serpentine microreactor. After the reaction has occurred in the microreactor 24 the analyte flows into the microfluidic channel 16 of the localized device of FIG. 1A where Raman measurements are made. The total volume of the mixing region 22, from the junction where reactants begin mixing to the Raman detection region was 8.83 μl.

The acid catalyzed esterification of ethanol with acetic anhydride to produce ethyl acetate was chosen as a model reaction to be monitored using the arrangement of FIG. 7. Sulphuric acid was used as the catalyst for the reaction, a minute amount of which was added into the reactants prior to the reaction. All the reagents used (Sigma Aldrich) were of ACS reagent quality. The reaction was carried out at room temperature ~22° C. The solutions were pumped into the microreactor using syringe pumps (Harvard Apparatus). The stoitiometric ratio of acetic anhydride to ethanol is 1:2, which would be 1:3.24 in volume. The ratio of the flow rates of the reactants was fixed to be 1:4 since ethanol was the carrier solvent. The dynamics of the chemical reaction were studied at different analyte flow rates.

Figure 8A:
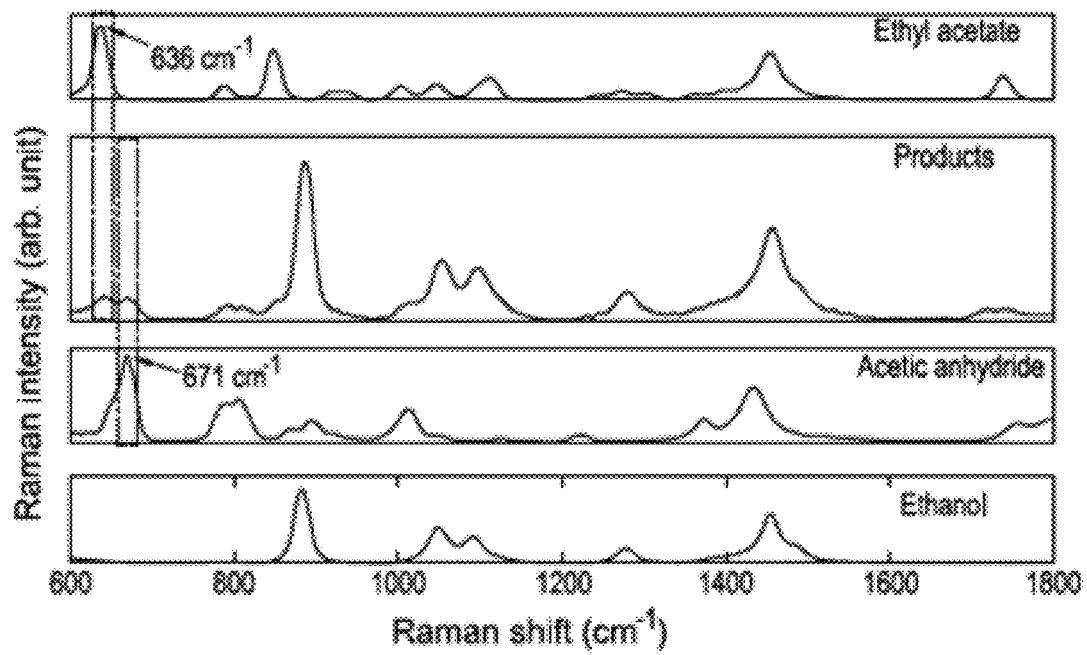
FIG. 8A shows various Raman spectra.

The progress of reaction at different interaction time scales was studied. By changing the total flow speed, the interaction time for the two reactants was varied. Interaction time was the time duration for the analyte to flow from the "T" junction, where the analytes were combined, to the Raman detection region. Prior to the actual experiment, the pure spectra of the reactants (acetic anhydride and ethanol) and product (Ethyl acetate) were obtained using the device of FIG. 1A and compared with the spectra of analyte for an incomplete reaction as shown in FIG. 8A. Since the product analyte had an incomplete reaction, the Raman peaks corresponding to all reactants and products could be seen. The Raman spectra shown in FIG. 8A were smoothed using Savitzky-Golay smoothing filter and baselined using iterative modified polynomial fitting. From the spectra, it is clear that the Raman peak at 671 $cm^{-1}$ for acetic anhydride and the Raman peak at 636 $cm^{-1}$ for ethyl acetate would be two representative peaks to be monitored to study the progress of the chemical reaction in the microreactor. The concentration of ethanol was not monitored as it was the carrier solvent. The total flow rate of the analyte was varied in order to change the interaction time of the reactants. Raman spectra of the analyte were obtained using WLRS with an acquisition time of 2 s.

Figure 8B:
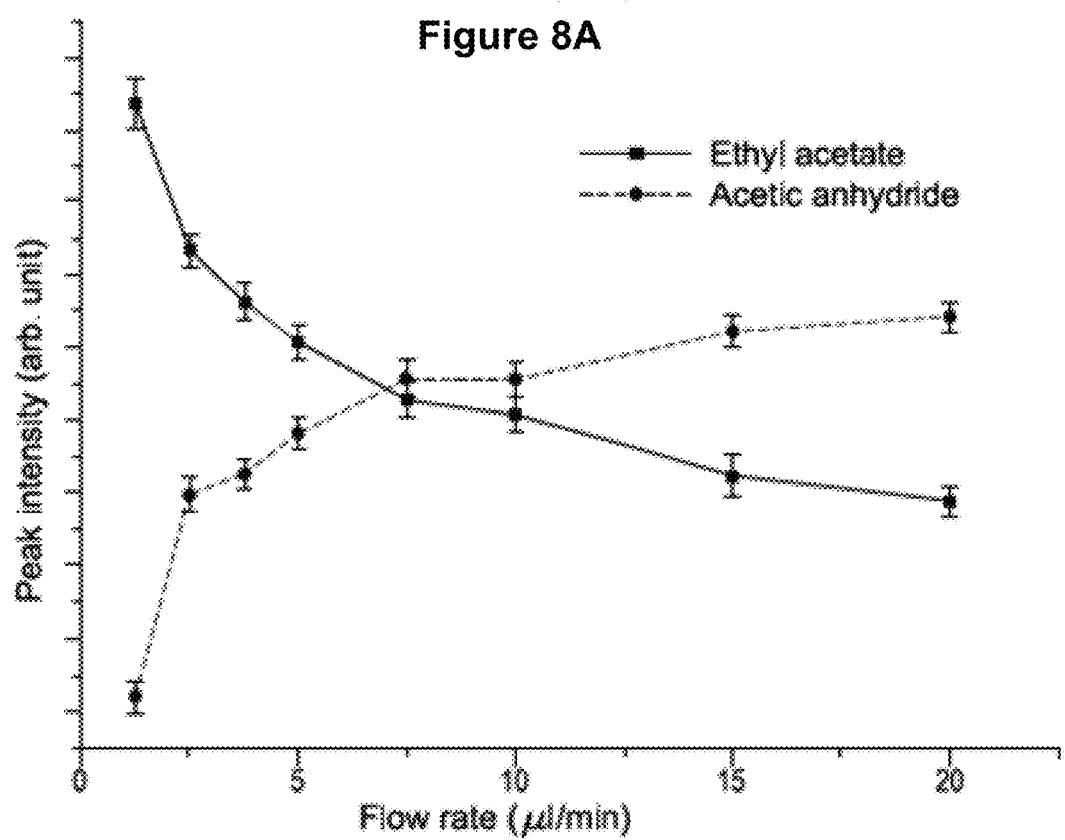
FIG. 8B shows a plot of peak intensity versus flow rate for two chemicals introduced into the micro-reactor of FIG. 7.

FIG. 8B shows the variation in the concentration of ethyl acetate and acetic anhydride with respect to the change in flow rate. Each data point is an average of 40 Raman spectra. Savitzky-Golay smoothing was done on the Raman spectra as a post processing step before estimating the peak intensity value. At low flow rates, the reaction was completed within the interaction time and the peaks corresponding to acetic anhydride were missing from the recorded Raman spectra. However, for higher flow rates the reaction was incomplete so that the acetic anhydride peak was visible in the Raman spectra and the intensity of the peak corresponding to ethyl acetate decreased. The recorded spectra were completely free from any background from the substrate of the microfluidic chip and there was no requirement for any optical alignment during the experiment.

Figure 9A:
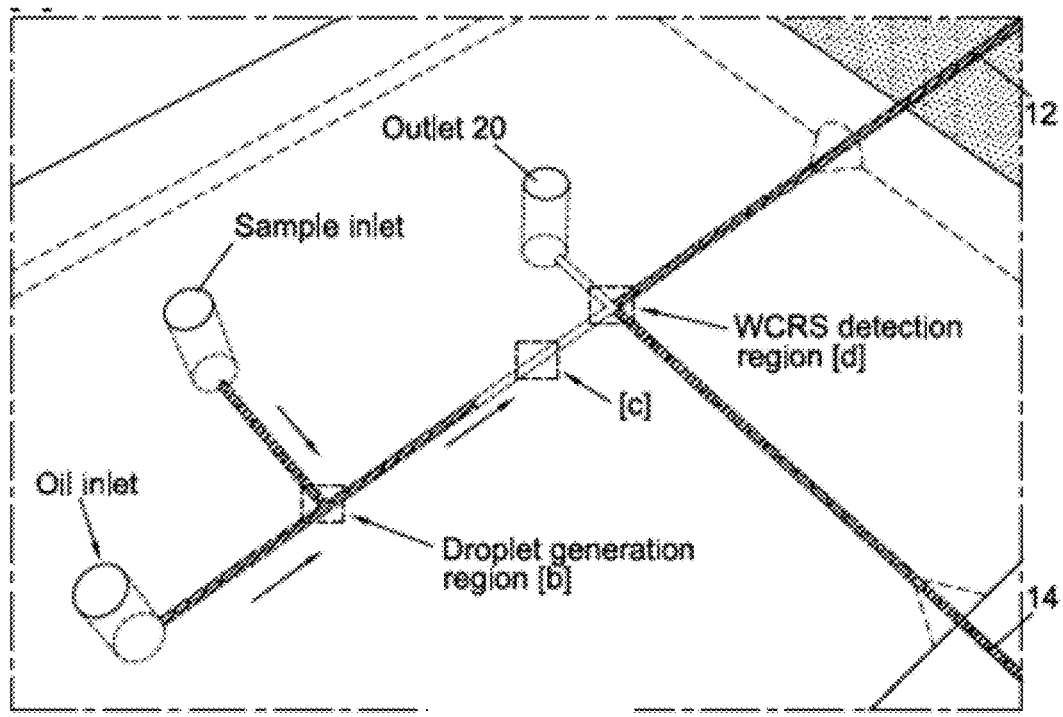
FIG. 9A is a view of a micro-droplet system integrated with the device of FIG. 1A.
Figure 9B:
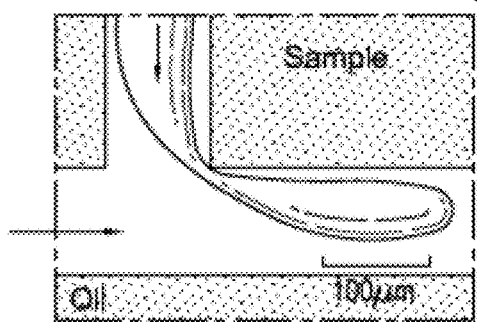
FIG. 9B is a detailed view of a T-junction where the sample and the oil buffer meet at right angles in the micro-droplet system depicted in FIG. 9A.
Figure 9C:
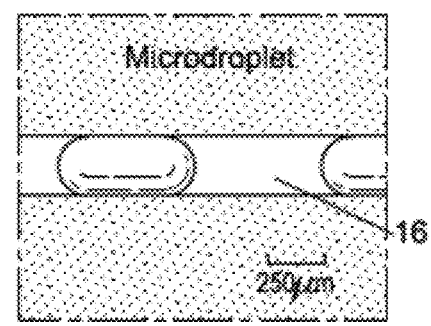
FIG. 9C is a detailed view of a section of microfluidic channel located downstream of the T-junction shown in FIG. 9B showing micro-droplets in the micro-droplet system depicted in FIG. 9A.

The device 10 of the invention can be incorporated in numerous microfluidic systems and arrangements. FIGS. 9A-9D show another example Here, the device of FIG. 1A is incorporated with a microdroplet based microfluidic system. There are two popular geometries for the creation of nanoliter sized droplets: the 'T-junction' and 'flow focusing'. FIG. 9A shows a simple T-junction design where the sample and an oil buffer meet at right angles for the droplet formation, as shown in FIG. 9B. When the two immiscible phases meet at the junction, the oil flow exerts a shearing force on the sample flow, which causes it to break into discrete microdroplets. By adjusting the relative flows of the two immiscible phases, droplets of various sizes can be formed from a single microfluidic chip as shown in FIG. 9C.

To test the arrangement of FIG. 9A, a system was prepared in which the droplet generation region in the microfluidic chip had a rectangular cross section with a width of 100 μm and height of 50 μm. Further downstream, the microfluidic channel widened into a channel with a circular cross section of diameter 250 μm, where the Raman spectra were collected. Ethanol diluted to 50% using de-ionized water was used as the sample. Droplets of ethanol were created within a continuous phase of silicone oil (Sigma Aldrich) containing Span 85 (Fluka) surfactant mixed at a volume ratio of 9.7:0.3.

Figure 9D:
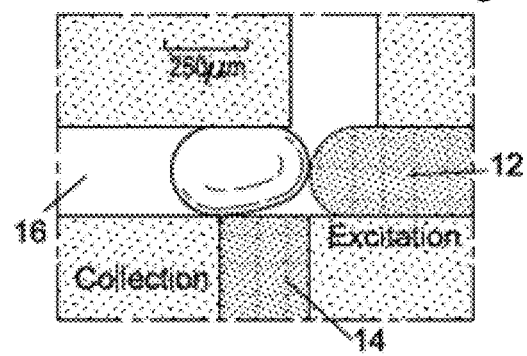
FIG. 9D is a detailed view of a Raman detection region of the microfluidic channel of the micro-droplet system depicted in FIG. 9A.

Droplets were imaged using a high speed camera (Fastec Troubleshooter) at 250 frames per second at three regions of interest: the T-junction, downstream and at the Raman detection region (FIGS. 9B, 9C, 9D respectively). The droplet volume was calculated by approximating its shape within the round channel to a cylinder and two partial ellipsoids representing the curved 'head' and 'tail'. At a flow ratio of 1:1 and flow rates of 120 μL/hr, the droplet volume was ~18.5 nL. Raman spectra were collected for an acquisition time of is which amounts to 1.8 droplets passing through the detection region per acquisition.

Figure 10:
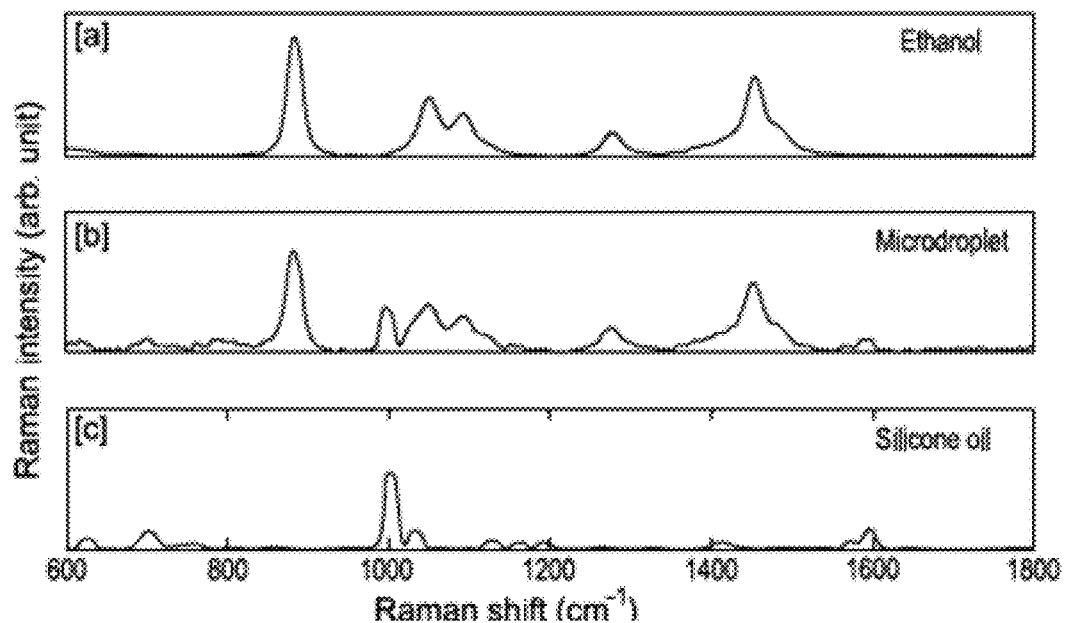
FIG. 10 shows Raman spectra collected in the microdroplet generation channel of the system of FIG. 9 with an acquisition time of is compared with that of the pure spectra of oil and ethanol.

FIG. 10 shows the Raman spectra collected from the system of FIG. 9A with an acquisition time of 1s, as well as the pure spectra of oil and ethanol. The spectra were smoothed using a Savitzky-Golay polynomial and baselined. It can be seen that the major peak in the Raman spectra of ethanol is clearly visible in the spectra along with the peaks for oil. For the flow rates used, during a period of 1 s, 1.8 droplets passed through the Raman analysis region. However, it is possible to reduce the acquisition time further. Hence, in principle it would be possible to use the device of the invention for probing a single droplet in a microdroplet based microfluidic system. This detection scheme could easily be incorporated into any microdroplet system to probe and study various chemical and physical dynamics.

The device of the invention has numerous advantages, making it suitable for many applications that to date have not been commercially practical. For example, the device can be used to capture and analyze Raman signals from alcoholic beverages. In particular, various different brands of Scotch whiskies have been investigated. Raman spectra of these whisky samples were obtained and various multivariate techniques were used for achieving concentration prediction and classifications of different types of Scotch whisky. Partial Least Square (PLS) calibration was performed to obtain the concentration of various brands of whisky. Further, principal component analysis (PCA) was used to classify various brands based on flavor, age and cask.

For the whisky tests, the microfluidic chip was fabricated in PDMS using soft lithography with pre-defined fiber insertion channels. Two ultra-low-OH multimode optical fibers with core size 200 μm (Polymicro Technologies) were embedded into the chip for the excitation and collection of Raman signals. The whisky samples were directly loaded into the microfluidic chip without any special sample preparation stage. A drop of whisky of volume 20 μl was placed at the sample inlet using a micropipette. This sample was then sucked into the microfluidic channel using a 1 ml syringe attached to the outlet of the microfluidic chip. Once the sample was sucked into the signal detection region, Raman spectra of the sample were acquired with a 2 s acquisition time.

After the acquisition was completed, any remaining sample at the sample inlet was wiped off and 40 μl of deionized water was placed at the sample inlet, which was passed through the microfluidic channel to rinse the system. It was ensured that the rinsing procedure was sufficient to avoid any cross contamination while acquiring spectra from different samples. After the rinsing procedure, the chip was ready for use with a new sample. With a 2 s acquisition time, the total time required to acquire a Raman spectrum from the sample was less than 1 minute, including the sample loading procedure as described.

Raman excitation was performed with 200 mW of laser power coupled to a multimode excitation fiber through an SMA adaptor from a diode laser (Laser2000 (UK) Ltd., maximum power 450 mW, wavelength 785 nm). The other end of the collection fiber coupled the collected Raman photons into a spectrometer (Shamrock SR-303i, Andor Technology) through a telescopic system to match the F-number of the fiber to that of the spectrometer. The spectrometer employed a 400 lines/mm grating, blazed at 850 nm and was equipped with a deep depletion, back-illuminated and thermoelectrically cooled CCD camera (Newton, Andor Technology) for the detection of Raman signal.

Six commercially available Scotch whisky brands and their variants were used in this study. For the ethanol concentration calibration experiment, ethanol samples with known concentration in percentage volume were prepared by mixing 100% pure ethanol (Sigma Aldrich) with deionized water. To avoid experimental bias, four sets of samples with ethanol concentration in percentage volume varying from 36% to 43% with a step size of 1% were prepared by two different people. Five spectra from each of the sets for each concentration were acquired with an acquisition time of 2 s each, leaving 20 spectra corresponding to each concentration.

For the classification experiments, the fluorescent background was also taken into consideration along with the Raman signals. To avoid the effect of photo-bleaching skewing the classification results, the spectra were acquired after ensuring that the samples were photo-bleached by irradiating the sample with the excitation laser beam for five minutes.

For the classification experiments, four sets of 50 Raman spectra each were obtained from one type of photo-bleached whisky sample. A series of Raman spectra of non-photo-bleached samples were also obtained for 800 s, with 2 s acquisition time for each spectra, to classify whisky samples from same brand with different flavors which was otherwise not possible to classify.

The Raman spectra of the whisky samples mainly contain the peaks corresponding to ethanol which amounts to 40% of the sample volume. The acquisition parameters used in this experiment were not sufficient to obtain specific peaks corresponding to the congeners which amount to only less than 5% of the total volume. However, these vary the fluorescence background of the acquired Raman spectra. This information when combined with the Raman peaks was crucial to assist in classification of different types of whiskies. This will be explained in more detail later.

Figure 11:
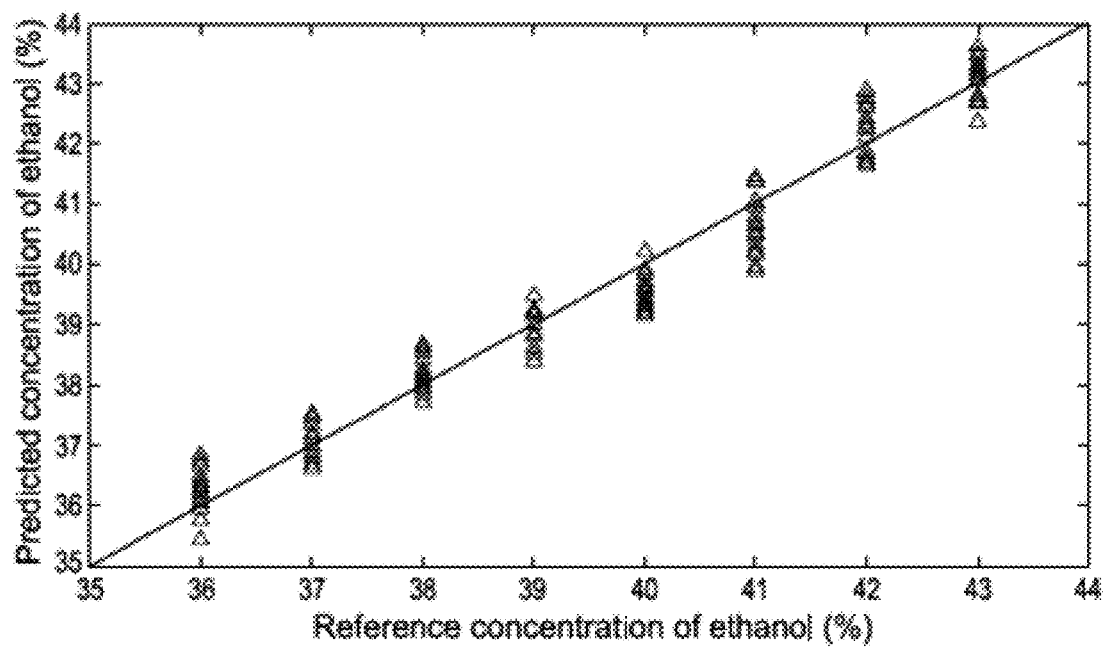
FIG. 11 is a plot of predicted concentration of ethanol versus a reference concentration of ethanol for validation of a PLS model.

A PLS model was used to predict the concentration of the ethanol content in the whisky sample. The model was built based on the Raman spectra from 655 cm−1 to 1720 cm−1 of samples with known ethanol concentration. For each concentration, 20 Raman spectra were used. The Raman spectra were smoothed using a Savitzky-Golay smoothing filter and baselined using iterative modified polynomial fitting (impf) to remove the fluorescence background from the data. The model was validated with a "leave one out" cross validation method as shown in FIG. 11. When six parameters were used for prediction, the root mean square error of prediction (RMSEP) was 1.17%.

Figure 12:
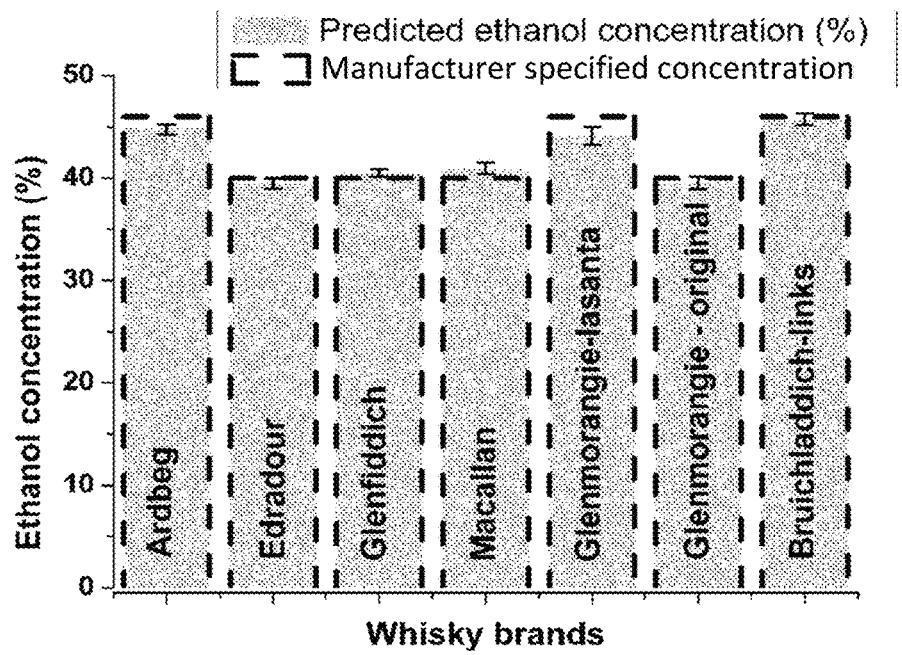
FIG. 12 is a graph showing predicted ethanol concentration in various whisky brands using a PLS model.

The validated PLS model was used to predict the ethanol concentration of seven types of whisky. The model could predict the ethanol concentration of the whisky samples within 1% of error in predicted concentration when compared to the concentration of ethanol claimed by the manufacturers in the label of the product as shown in FIG. 12. From the prediction result, it is clear that the PLS model works reasonably well for predicting ethanol concentration of whisky sample. Ethanol concentration is an important parameter in the assessment of the quality of whisky. The ethanol concentration has to be more than 40% for authentic whisky samples. Hence, this calibrated technique may be used for rapid detection of counterfeit whisky samples.

Although the acquired Raman spectra of whisky contain only the Raman peaks corresponding to ethanol, the fluorescent background in the acquired Raman spectra was different for different types of whisky samples. This may result from the varying contribution of the congener components that are responsible for the color of the whisky. For the ethanol concentration prediction, the fluorescence background of the acquired Raman spectra was discarded by performing baseline subtraction on the data. However, the information of the fluorescent background proved useful for categorizing different types of whiskies. Hence, for the classification of the whisky samples, PCA was performed on acquired Raman data just after Savitzky-Golay smoothing.

Figure 13:
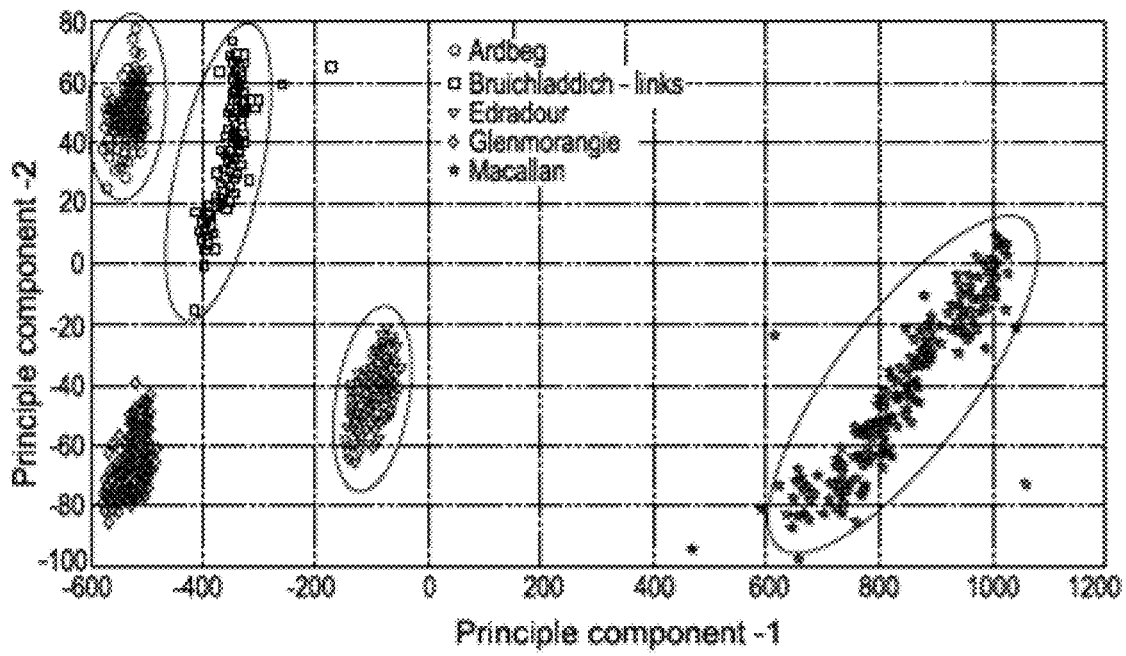
FIG. 13 is a PC1 vs. PC2 cluster plot of Raman spectra of various whisky samples, each consisting of 200 spectra acquired from photo-bleached whisky samples.

There are various types of classifications proposed for single malt Scotch whisky based on flavor, geographical location of origin, age, cask etc. PCA based multivariate analysis was used to cluster the Raman spectra obtained from different types of whisky samples. Different whisky brands were clustered and the result was compared with a popular classification of single malt whisky based on their aromatic features. Various brands of Scotch whiskies were classified into ten clusters in this classification. There is a smooth transition in the quality of whiskies from A to J. This means the aromatic features of the brands in cluster A and cluster B would be similar and that of cluster A and cluster J would be very different. PCA was applied to the Raman spectra acquired from five ten year old whisky brands. After performing PCA, the data was plotted in a graph of principal component 1 (PC1) vs. principal component 2 (PC2) as shown in FIG. 13. The samples used were from clusters A, B, H, I and J. It was observed that each samples formed a cluster distinguishable from each other. Also, the samples which corresponds to the clusters H, I and J were closer when compared to the samples corresponds to A and B. This shows that the acquired spectra show a trend to clustering based on the aromatic feature of the whisky sample.

Figure 14:
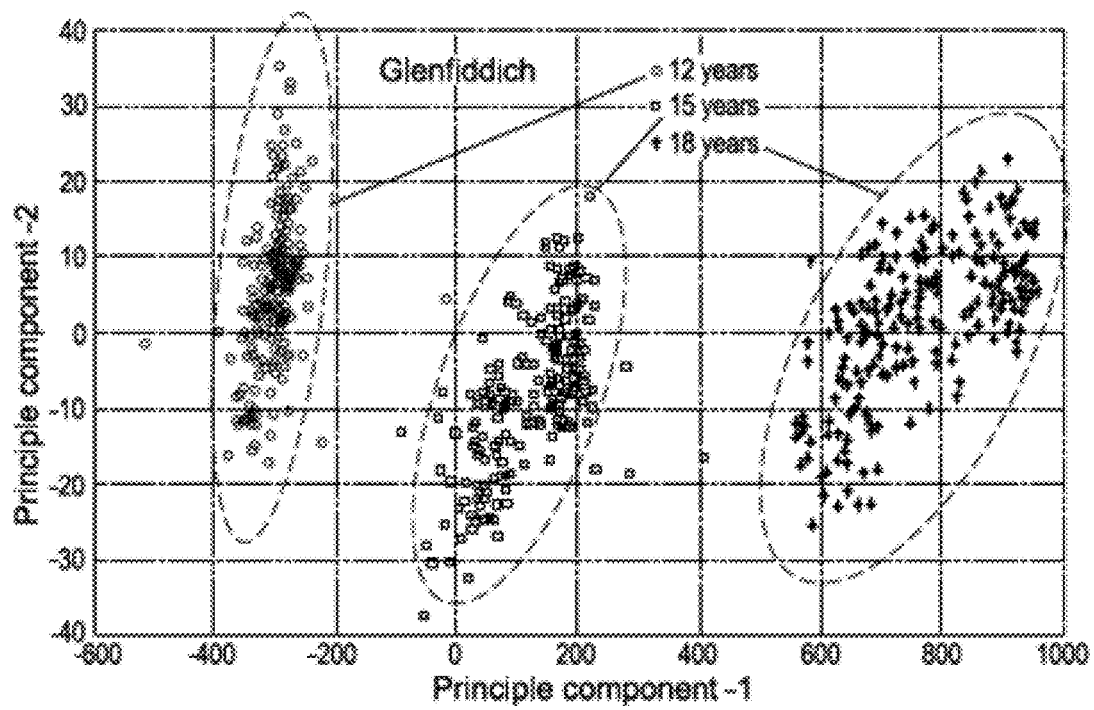
FIG. 14 is a PC1 vs. PC2 cluster plot for three samples of the same brand of whisky, but with different ages.

Another key criterion to classify whisky is its age. The aging process changes the congener profile and color of the whisky samples. PCA was applied to Raman spectra obtained from three whisky samples of the same brand ('Glenfiddich') with different ages. As can be seen in FIG. 14, the Raman spectra of the samples corresponding to different ages are clearly distinct from one other.

Figure 15:
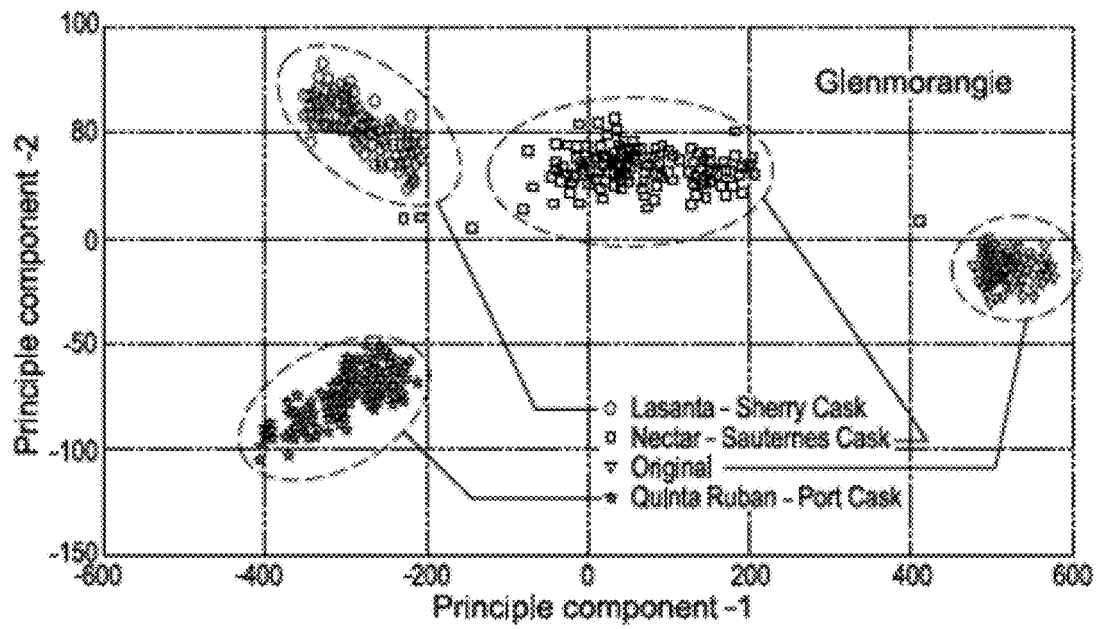
FIG. 15 is a PC1 vs. PC2 cluster plot for four samples of the same brand of whisky sample, but matured in different casks.

Classification of whisky samples based on their cask was also investigated. Four types of 10 year old "Glenmorangie" were chosen where the whisky was kept in different cask for the final two years of the maturing process. The difference in the cask also alters the congener profile. The clustering was performed as explained before and the results shown in FIG. 15 shows a clear distinction between in the PC1 vs. PC2 plot.

Figure 16:
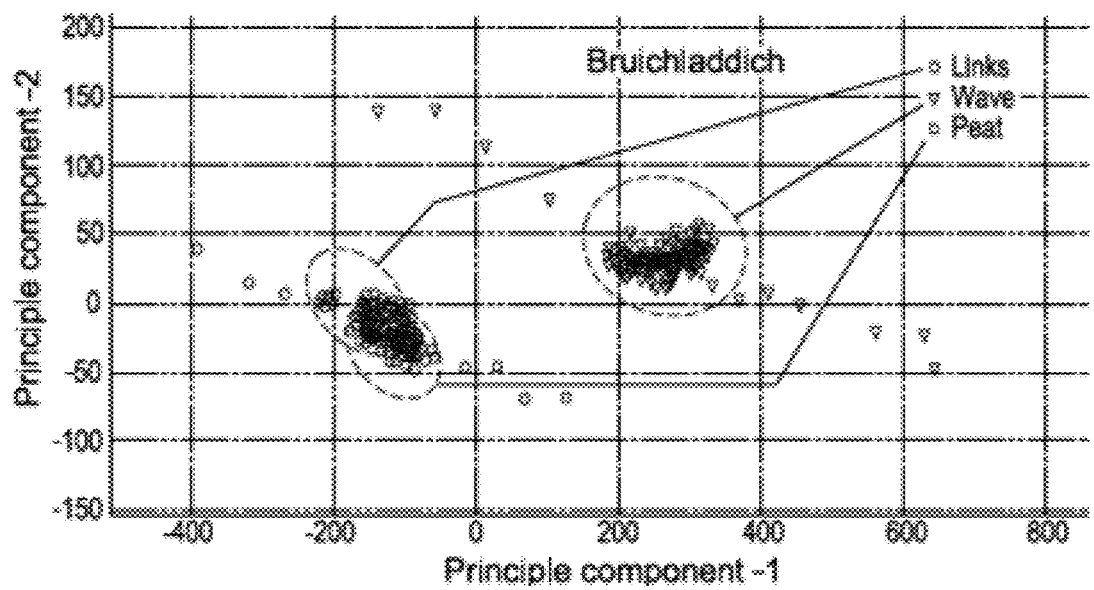
FIG. 16 is a PC1 vs. PC2 cluster plot for three samples of the same brand of whisky, but with different aromatic features.
Figure 17:
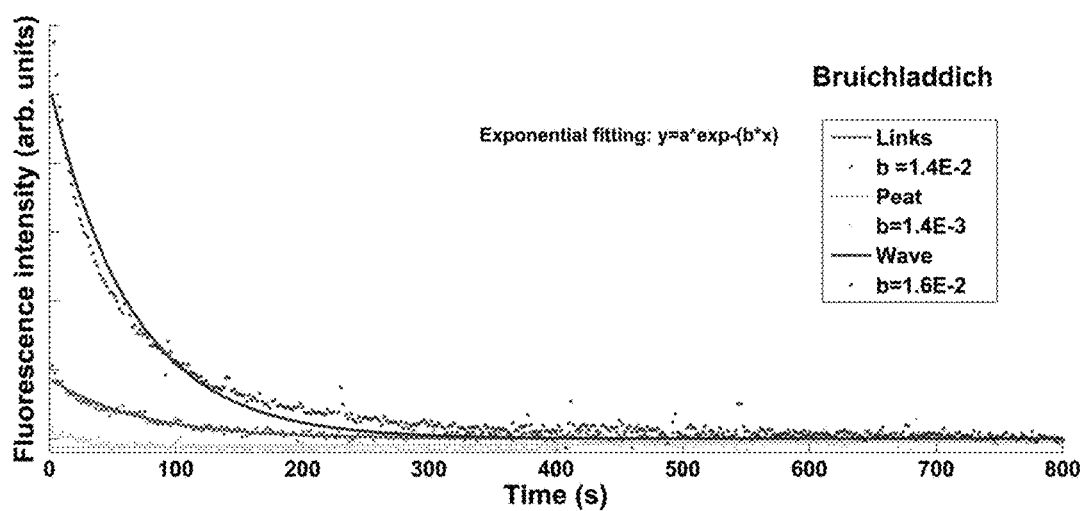
FIG. 17 is a plot of fluorescence intensity versus time for three whisky samples to investigate the effects of photo-bleaching.

Another set of samples of same brand ("Bruichladdich") with different aromatic features were classified as shown in FIG. 16. It can be seen that "Links" and "Peat" are not distinguishable using PCA based clustering. This means the information from the Raman spectra and fluorescent background was not sufficient to distinguish between these two types of whiskies. A solution to this problem was to use the information on the rate of photo-bleaching to distinguish between these particular samples. In order to obtain this information, a series of Raman spectra were acquired with 2 s acquisition time for 800 seconds each for each samples. The fluorescence decay due to photo-bleaching was obtained by plotting the average signal level in the region between 740 cm−1 to 750 cm−1 where no Raman peak was present. The obtained curve was fitted to a single decaying exponential to obtain the decay constant as shown in FIG. 17. It can be seen that the decay constant corresponding to "Links" is one order greater than that of "Peat". When compared to previous methods were sample detection was possible with 2 s acquisition, obtaining decay constant is time consuming (with required acquisition time ~6 minutes). However this gives additional information which can help to achieve classification.

The present invention provides a completely alignment-free optofluidic device for Scotch whisky analysis. By harnessing the advantages of optofluidics, the present invention offers portability and fast detection of analyte with relatively low acquisition time (2 s) with very low required sample volume (20 μl). In this device, samples can be analyzed without any special sample preparation stage. Furthermore, the combination of Raman spectra and the fluorescent background information can be used to classify different types of whiskies using PCA. Classification of whiskies based on its aromatic features, age and cask was achieved. It was also demonstrated that the fluorescence decay constant can be also used as another parameter to distinguish whisky types which are non-distinguishable otherwise although this required a longer acquisition time. The result shows that this optofluidic Raman probe is well suited for developing portable devices to authenticate alcoholic beverages. The low acquisition time also offers development of devices for online process monitoring in production lines of liquors.

The device of the present invention uses embedded waveguides in a microfluidic chip for measuring Raman signals. This device is scalable and easily adaptable to various microfluidic architectures and allows alignment free and fast acquisition of Raman spectra of analytes without any background from the substrate of the microfluidic chip. The divergent beam used for Raman excitation allows the sampling volume in the microfluidic channel to be maximized. The device allows sensitive analyte detection with minimal sample preparation.

The minimum detection limit of this device for this device to detect urea was estimated to be 80 mM for an acquisition time of 5 s with 200 mW excitation power which is better than its probe based counterpart. Also the device could be easily combined with other microfluidic designs in order to extend its functionality. The simple and robust design of the device of the invention opens the way for Raman spectroscopy to become a practical and desirable analyte detection method in microfluidics.

A skilled person will appreciate that variations of the disclosed arrangements are possible without departing from the invention. For example, the excitation waveguide and/or the collection waveguide may be coated with an optically active material. In particular, the end of the excitation waveguide and/or the collection waveguide may be coated with a filter material. In the case of the excitation waveguide, the filter material may be selected to allow only the excitation wavelength through. In the case of the collection waveguide the filter material may be selected to block the excitation wavelength. In addition, the end of at least one of the excitation waveguide and/or the collection waveguide may be shaped. Accordingly the above description of the specific embodiment is made by way of example only and not for the purposes of limitation. It will be clear to the skilled person that minor modifications may be made without significant changes to the operation described.

What is claimed is:

1. A method for analyzing alcoholic beverages, the method comprising:
   illuminating a sample of a beverage of unknown type and unknown alcohol concentration using light suitable for stimulating a Raman signal;
   capturing light emitted from the illuminated sample, the light emitted from the illuminated sample including the Raman signal and fluorescent light;
   obtaining a spectrum of the captured light; and
   analyzing the beverage by:
      using principal component analysis of the spectrum of the captured light, including both the Raman signal and the fluorescent light to determine a classification of the beverage;
      removing a fluorescent background from the spectrum of the captured light to provide a Raman spectrum;

determining a percentage alcohol concentration of the beverage from the Raman spectrum; and authenticating the beverage based on the determined classification of the beverage and the determined percentage alcohol concentration of the beverage.

2. A method as claimed in claim 1, wherein the classification of the beverage is based on at least one of type, flavor, aromatic features, geographic origin, brand, age and cask.

3. A method as claimed in claim 1, further comprising calibrating the percentage alcohol concentration measurement using a known alcohol.

4. A method as claimed in claim 1, further comprising calibrating the percentage alcohol concentration measurement using ethanol.

5. A method as claimed in claim 1, wherein determining the percentage alcohol concentration of the beverage from the Raman spectrum comprises determining the percentage alcohol concentration using a partial least squares model.

6. A method as claimed in claim 1 comprising photo-bleaching the beverage sample prior to measuring the Raman signal.

7. A method as claimed in claim 1 wherein analyzing the beverage comprises detecting counterfeit beverage.

8. A method as claimed in claim 1, wherein the beverage comprises whisky.

9. A method as claimed in claim 1, wherein analyzing the beverage comprises classifying the beverage at least in part according to a rate of decay of the fluorescent light resulting from photo-bleaching of the sample of the beverage, wherein the sample of the beverage consists only of the beverage.

10. A system for analyzing alcoholic beverages, the system comprising:
a portable device having a sample chamber for receiving a sample of a beverage of unknown type and unknown alcohol concentration;
a light source configured to illuminate the sample of the beverage to stimulate a Raman signal; and
a detector configured to capture light emitted from the illuminated sample, the light emitted from the illuminated sample including the Raman signal and fluorescent light,
wherein the system is configured to obtain a spectrum of the captured light and analyze the beverage by:
using principal component analysis of the spectrum of the captured light including both the Raman signal and the fluorescent light to determine a classification of the beverage;
removing a fluorescent background from the spectrum of the captured light to provide a Raman spectrum;
determining a percentage alcohol concentration of the beverage from the Raman spectrum; and
authenticating the beverage based on the determined classification of the beverage and the determined percentage alcohol concentration of the beverage.

11. A system as claimed in claim 10 wherein the system is adapted to analyze the beverage to classify the beverage based on at least one of type, flavor, aromatic features, geographic origin, brand, age and cask.

12. A system as claimed in claim 10 wherein the system is adapted to calibrate the percentage alcohol concentration measurement using a known alcohol.

13. A system as claimed in claim 10 wherein the system is adapted to calibrate the percentage alcohol concentration measurement using ethanol.

14. A system as claimed in claim 10 wherein determining the percentage alcohol concentration of the beverage from the Raman spectrum comprises using a partial least squares model.

15. A system as claimed in claim 10 adapted to photo-bleach the beverage sample prior to measuring the Raman signal.

16. A system as claimed in claim 10 wherein the system is adapted to analyze the beverage to detect counterfeit beverage.

17. A system as claimed in claim 10, wherein the beverage comprises whisky.

18. A system as claimed in claim 10, adapted to photo-bleach the sample of the beverage, measure a decay of the fluorescent light as a result of the photo-bleaching of the sample of the beverage, and analyze the beverage by classifying the beverage at least in part according to a measured rate of decay of the fluorescent light resulting from the photo-bleaching of the sample of the beverage, wherein the sample of the beverage consists only of the beverage.

* * * * *